US012582603B2

(12) United States Patent
Karavas et al.

(10) Patent No.: US 12,582,603 B2
(45) Date of Patent: Mar. 24, 2026

(54) OPHTHALMIC PHARMACEUTICAL COMPOSITION CONTAINING A COMBINATION OF BRINZOLAMIDE AND BRIMONIDINE AND METHOD OF PREPARATION THEREOF

(71) Applicant: NTC S.r.l., Milan (IT)

(72) Inventors: Evangelos Karavas, Pallini (GR); Efthymios Koutris, Pallini (GR); Vasiliki Samara, Pallini (GR); Ioanna Koutri, Pallini (GR); Anastasia Kalaskani, Pallini (GR); Andreas Kakouris, Pallini (GR); Rumit Rajivbhai Shah, Pallini (GR)

(73) Assignee: NTC S.r.l., Milan (IT)

( * ) Notice: Subject to any disclaimer, the term of this patent is extended or adjusted under 35 U.S.C. 154(b) by 345 days.

(21) Appl. No.: 16/761,337

(22) PCT Filed: Nov. 6, 2018

(86) PCT No.: PCT/EP2018/025282
§ 371 (c)(1),
(2) Date: May 4, 2020

(87) PCT Pub. No.: WO2019/091596
PCT Pub. Date: May 16, 2019

(65) Prior Publication Data
US 2021/0177753 A1 Jun. 17, 2021

(30) Foreign Application Priority Data
Nov. 7, 2017 (GR) .............................. 20170100500

(51) Int. Cl.
| *A61K 9/08* | (2006.01) |
| *A61K 9/00* | (2006.01) |
| *A61K 31/498* | (2006.01) |
| *A61K 31/542* | (2006.01) |
| *A61K 47/02* | (2006.01) |
| *A61K 47/10* | (2017.01) |
| *A61K 47/32* | (2006.01) |
| *A61K 47/34* | (2017.01) |

(52) U.S. Cl.
CPC .............. *A61K 9/08* (2013.01); *A61K 9/0048* (2013.01); *A61K 31/498* (2013.01); *A61K 31/542* (2013.01); *A61K 47/02* (2013.01); *A61K 47/10* (2013.01); *A61K 47/32* (2013.01); *A61K 47/34* (2013.01)

(58) Field of Classification Search
CPC ...... A61K 9/08; A61K 9/0048; A61K 31/498; A61K 31/542; A61K 47/10
See application file for complete search history.

(56) References Cited

U.S. PATENT DOCUMENTS

| 5,282,971 A * | 2/1994 | Degen ..................... A61P 27/02 |
| | | 210/500.37 |
| 6,503,497 B2 * | 1/2003 | Chowhan ............. A61K 9/0048 |
| | | 424/427 |
| 2010/0324031 A1 | 12/2010 | Kabra |
| 2011/0098354 A1 * | 4/2011 | Jimenez-Bayardo ... A61P 27/06 |
| | | 514/530 |
| 2015/0224196 A1 | 8/2015 | Kabra |
| 2016/0324967 A1 * | 11/2016 | Kabra .................... A61K 47/36 |

FOREIGN PATENT DOCUMENTS

| EP | 2 254 549 B1 | 11/2013 | |
| EP | 2 442 790 B1 | 3/2014 | |
| EP | 2 364 137 B1 | 3/2017 | |
| WO | WO 2010/0148190 A1 | 12/2010 | |
| WO | WO-2017099207 A1 * | 6/2017 | ................ A61J 1/05 |
| WO | WO 2017/217450 A1 | 12/2017 | |

OTHER PUBLICATIONS

English machine translation of WO 2017/099207 A1 made Mar. 10, 2022. (Year: 2022).*
English machine translation of Table 1 of WO 2017/099207 A1 made Aug. 26, 2022. (Year: 2022).*
International Search Report issued Feb. 14, 2019 in PCT/EP2018/025282 filed on Nov. 6, 2018.
Greek Office Action issued on Nov. 9, 2018 in Greek Patent Application No. 20170100500 (with English translation of Categories of Cited Documents), 2 pages.

* cited by examiner

*Primary Examiner* — Michael B. Pallay
(74) *Attorney, Agent, or Firm* — Oblon, McClelland, Maier & Neustadt, L.L.P.

(57) ABSTRACT

The present invention relates to an ophthalmic aqueous composition for the decrease of intraocular pressure in patients with ocular hypertension or open angle glaucoma containing a combination of Brinzolamide and Brimonidine and a method for preparation thereof. The invention as currently presented has a significant advantage over ophthalmic compositions already known in the art. More particularly the present invention relates to a multi-dose ophthalmic aqueous composition comprising a borate, a single polyol and benzalkonium chloride as an antimicrobial agent.

19 Claims, No Drawings

OPHTHALMIC PHARMACEUTICAL COMPOSITION CONTAINING A COMBINATION OF BRINZOLAMIDE AND BRIMONIDINE AND METHOD OF PREPARATION THEREOF

TECHNICAL FIELD OF THE INVENTION

The present invention relates to an ophthalmic aqueous composition for the decrease of intraocular pressure in patients with ocular hypertension or open angle glaucoma containing a combination of Brinzolamide and Brimonidine and a method for preparation thereof. The invention as currently presented has a significant advantage over ophthalmic compositions already known in the art. More particularly the present invention relates to a multi-dose ophthalmic aqueous composition comprising a borate and a single polyol.

BACKGROUND OF THE INVENTION

Glaucoma is a degenerative disease of the eye, wherein elevated intraocular pressure disrupts normal eye function and results in irreversible damage to the optic nerve head and loss of visual function. In particular, a glaucoma patient will develop peripheral visual field loss followed by central field loss usually in the presence of elevated intraocular pressure, which if left untreated it may eventually lead to blindness.

Most patients with glaucoma are treated with topical medication that controls elevated ocular pressure. Medications most commonly used are α-adrenergic receptor agonists, epinephrine compounds, prostaglandins that reduce ocular pressure by increasing aqueous outflow, β-adrenergic receptor antagonists and carbonic anhydrase inhibitors that work by decreasing aqueous production. Even though the typical treatment regimen for lowering intraocular pressure is topical β-blockers, in the recent years the use of prostaglandins as initial therapy is increased.

Carbonic anhydrase inhibitors are also used for the treatment of ocular hypertension related to glaucoma. The drugs that belong to this family inhibit the enzyme carbonic anhydrase and thus, they reduce the contribution of the aqueous humor formation made by the carbonic anhydrase pathway. However, these drugs cannot be used via a systemic route because they would inhibit the enzymatic activity of carbonic anhydrase throughout the entire body. In general, the enzyme carbonic anhydrase plays a major role in regulating pH and fluid levels in the human body by converting carbon dioxide to carbonic acid and bicarbonate ions.

Targeting of the carbonic anhydrase inhibitor to the desired ocular tissue diminishes or even eliminates the side effects caused by the inhibition of carbonic anhydrase in the entire body, which can be as a severe as metabolic acidosis or less severe, like numbness, vomiting, tingling, general malaise and the like.

Brinzolamide is a well characterized carbonic anhydrase inhibitor with the chemical name R 4-ethylamino-3,4-dihydro-2-(3-methoxy)propyl-2H-thieno[3,2-e]-1,2-thiazin-6-sulfonamide1,1 dioxide that is characterized in U.S. Pat. No. 5,378,703. It is currently formulated in an ophthalmic suspension sold as Azopt®. U.S. Pat. No. 6,071,904 describe a process to manufacture Brinzolamide suspension by autoclaving Brinzolamide and surfactant together followed by ball milling. This milled mixture is then added to the rest of the excipients to form a final suspension.

α-adrenergic receptor agonists is another well characterized class of drugs used for the treatment of high intraocular pressure related with glaucoma. The drugs of this class act via decreasing synthesis of aqueous humor, and increasing the amount that drains from the eye through uveoscleral outflow.

Brimonidine is an α-adrenergic receptor agonists with the chemical name 5-Bromo-6-(2-imidazolidinylideneamino) quinoxaline L-tartrate and has been disclosed in U.S. Pat. No. 3,890,319. Bimonidine has been sold as ophthalmic solution under the name Alphagan® (now discontinued) and Alphagan P®. the later contains Brimonidine tartrate at two Brimonidine concentrations, 0.15% and 0.1%, each of which is lower than the 0.2% Brimonidine concentration in Alphagan®. Alphagan® P has a pH between 7.15 and 7.8. The preservative contained in Alphagan® P is chlorine dioxide. Alphagan® P also contains an anionic solubility enhancing component (carboxymethylcellulose) to help solubilize the brimonidine that is unionized at the pH of the compositions. The formulations have been described in U.S. Pat. Nos. 5,424,078 and 6,562,873.

When manufacturing a stable ophthalmic formulation to be administered topically to the eye, the solution needs to have specific characteristics, for example pH, osmolality, specific gravity and viscosity. Regulation of these characteristics through the selection of specific excipients will avoid any unwanted side effects such as visual blurring, burning sensation, low corneal contact and drying of the eye.

In particular, regulating the viscosity of the ophthalmic solution has the primary benefit of increasing the ocular contact time, thereby increasing the drainage rate and increasing drug bioavailability. A secondary benefit is a lubricant effect that is noticeable to many patients. In addition, viscosity serves to retard the settling of the particles between uses and at the same time maintains their suspension for uniform dosing.

When using a multi-dose product for ophthalmic use the exposure of the product to air after repeated use increases the risk of microbial contamination. It is therefore necessary to use a chemical agent that prevents the proliferation of microbes and other organisms in the composition, such an agent can be an antimicrobial preservative. Another way to reduce risk of contamination is the use of a packaging system that prevents or reduces the risk of microbes reaching the pharmaceutical composition. However, ophthalmic compositions may come into contact with the cornea either directly or indirectly. The cornea is particularly sensitive to exogenous chemical agents. Consequently, in order to minimize the potential for harmful effects on the cornea, it is preferable to use anti-microbial preservatives that are relatively non-toxic and in low concentrations.

When a patient is not able to control intraocular pressure with a monotherapy, a combination of drugs is necessary to provide the adequate control. This however, adds further difficulties in the development of the ophthalmic composition because the inventors need to take into account the specificities of both active agents. The present invention relates to a composition for topical administration to the eye of a patient of Brinzolamide and Brimonidine or pharmaceutically acceptable salts thereof a single polyol, borate and benzalkonium chloride as an antimicrobial agent. It is already known in the art that a multi-dose ophthalmic composition works well with two polyols, a borate and Benzalkonium chloride; however the inventors were able to minimize the amount of ingredients to a composition with a single polyol, a borate and benzalokinum chloride. This patent application provides an effective and safe topical ophthalmic pharmaceutical composition containing a combination of drugs which has increased stability, fewer side effects and requires a lower effective concentration of preservatives as compared to other ophthalmic solutions available in the market.

SUMMARY OF THE INVENTION

The main objective of the present invention is to develop a stable ophthalmic formulation that is free of microbes during storage and for the duration of use; such formulation would provide a significant improvement over the prior art formulations.

It is, therefore, an object of the present invention to provide a thermodynamically stable and efficient product comprising Brizolamide or a pharmaceutically acceptable salt thereof and Brimominide or pharmaceutically acceptable salt thereof for ophthalmic administration.

Another object of the present invention is to provide an ophthalmic formulation comprising Brinzolamide or pharmaceutically acceptable salts thereof and Brimonidine or pharmaceutically acceptable salts thereof and a polyol-borate system comprising of a single polyol and a borate, along with an antimicrobial agent. The formulation of the present invention can overcome problems that arise during manufacturing of ophthalmic formulations.

A further object of the present invention is to provide an aqueous pharmaceutical formulation comprising Brizolamide or a pharmaceutically acceptable salt thereof and Brimominide or pharmaceutically acceptable salt thereof for ophthalmic use that effectively addresses issues related to ocular tolerability in glaucoma patients.

In accordance with the above objects of the present invention, a process for the preparation of an aqueous ophthalmic formulation for topical administration containing Brinzolamide or a pharmaceutically acceptable salt thereof and Brimonidine or a pharmaceutically acceptable salt thereof together with a polyol-borate system and the minimum effective amount of an antimicrobial agent is also provided and it consists of the following steps:

Adding sodium chloride in water and stirring until complete dissolution

Adding a polyol and stirring until complete dissolution

Adding borate and stirring until complete dissolution

Adding Brinzolamide and stirring until complete dissolution

Adding Brimonidine and stirring until complete dissolution

Adding an antimicrobial agent and stirring until complete dissolution

Adjusting the pH, if necessary, with HCl/NaOH

Adjusting the final volume of the solution and stirring until complete dissolution;

Filtering the final solution through a 0.2μm filter;

Filling and sealing of vials.

Other objects and advantages of the present invention will become apparent to those skilled in the art in view of the following detailed description.

DETAILED DESCRIPTION OF THE INVENTION

The main object for the present invention is to provide a stable ophthalmic formulation suitable for topical administration to the eye containing Brinzolamide or pharmaceutically acceptable salt thereof and Brimonidine or a pharmaceutically acceptable salt thereof in combination with a polyol-borate system and an antimicrobial agent in an appropriate container.

For the purpose of the present invention, a pharmaceutical composition comprising an active agent or a combination of active agents is considered "stable" if said agent or combination of agents degrades less of more slowly than it does on its own or in known pharmaceutical compositions.

Ophthalmic suspensions are sterile, free form particles and especially prepared for instillation in the eye. Considerations in preparing ophthalmic solutions involve clarity, tonicity, pH/buffers, sterility, preservatives, antioxidants, viscosity enhancers and proper packaging.

Brimonidine has a pKa of 7.4. Hence, at pH below 6.6, it will be substantially ionized. For example, at a pH of 6.4, Brimonidine is about 90% ionized. It is well known that ionized ophthalmic drugs have greatly reduced ocular permeability. It would have been expected that at a pH below 6.6 or 6.5, Brimonidine would not permeate ocular tissue well, thereby reducing its efficacy compared to a higher pH product. It is believed that this is why the drug concentration in Alphagan® is substantially higher than in the higher-pH product Alphagan® P. The inventors have used a higher concentration of Brimonidine that should therefore be stable at a concentration of 6.5.

Ophthalmic compositions are generally formulated as isotonic, buffered solutions having pH between about 4.0 and 8.0. To achieve a pH in this range and to maintain the pH for optimal stability during the shelf life of the composition, a buffer is often included. Borate is the buffer of choice for use in ophthalmic compositions, since it has some inherent antimicrobial activity and often enhances the activity of antimicrobials.

The present invention is predicated upon the provision of one polyol in the presence of borate and benzalkonium chloride (BAC) for providing a pharmaceutical composition and particularly an ophthalmic composition that exhibits desired anti-microbial activity. Thus, the ophthalmic composition typically includes one polyol, BAC and borate As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts.

Generally, it is contemplated that various amounts of borate can be included in the ophthalmic compositions of the present invention. However, it has been found that lower concentrations of borate in combination with polyol can produce unexpectedly superior antimicrobial activity. Typically, for the present invention, the borate is at least about 0.05% w/v, more typically at least about 0.1% w/v and still more typically at least about 0.20% w/v of the ophthalmic composition. Furthermore, the borate can advantageously be less than about 1.0% w/v, more typically less than about 0.75% w/v and still more typically less than about 0.6% w/v of the ophthalmic composition.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to mannitol, glycerin, xylitol, sorbitol and propylene glycol.

In another preferred embodiment, the single polyol is entirely mannitol or sorbitol. Of these, it typically preferred that the polyol be entirely mannitol. The polyol is typically from at least about 1% w/v to about 5% w/v, more preferably from at least about 2% w/v to about 4% w/v of the ophthalmic composition. The polyol is most preferably from about 2.4% w/v to about 3.5% w/v of the ophthalmic composition.

The borate/polyol systems described herein may be included in various types of pharmaceutical compositions to enhance anti-microbial activity and preservation of the compositions, such as ophthalmic, otic, nasal and dermatological compositions, but is particularly useful in ophthalmic compositions. Examples of such compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of ophthalmic compositions, such as ocular lubricating products, artificial tears, astringents, and so on. The compositions may be aqueous or non-aqueous, but will generally be aqueous.

Ophthalmic solutions are ordinarily buffered at a pH that ensures maximum stability for the drugs they contain. The buffers are included to minimize any change in pH during storage which will affect the stability and solubility of the drug. pH in the range of 4.0 to 8.0 is considered optimum for ophthalmic solutions. Suitable pH adjusting agents include, but are not limited to, dibasic sodium phosphate, monobasic sodium phosphate, hydrochloric acid, sodium hydroxide, sodium hydrogen carbonate. Sodium hydroxide or hydrochloric acid are the buffers of choice in the present invention and the pH ranged from 3.0 to 8.0, most preferably 4.4 to 7.5 and most preferably the pH is 6.5.

Tonicity plays an important role in successful administration of an aqueous solution and it refers to the osmotic pressure exerted by salts in the solution. A solution acceptable for ophthalmic administration is required to be isotonic to lacrimal fluid with a tonicity value of 0.9% sodium chloride and an osmolality of 280 mOsm/kg. Tonicity agents used can be selected form, but are not limited to, sodium chloride, mannitol, dextrose, glycerine and potassium chloride, calcium chloride, magnesium chloride propylene glycol, glycerol. Sodium chloride is the preferred tonicity agent. The ophthalmic composition according to the present invention comprises from 0.6% to 1.1% (w/v) of sodium chloride, preferably from 0.8% to 0.9% (w/v) of sodium chloride. Furthermore the osmolality of the ophthalmic composition is in the range of 200 to 450 mOsm/Kg, more preferably 230 to 360 mOsm/kg.

Solutions intended for ophthalmic use must be sterile. Dry heat, steam under pressure and gas sterilization are common, however they might result in degradation of the active ingredient. Therefore sterilization via aseptic filtration was the method preferred in the present invention. Several types of filter are available including, but not limited to, hydrophilic polyvinylidene fluoride, hydrophilic modified polyvinylidene fluoride, polyethersulfone, double polyethersulfone, hydrophilic modified polyethersulfone, hydrophilic polytetrafluoroethylene, N66 posidyne. It was determined that a 0.2 μm hydrophilic polyvinylidene fluoride (PVDF) filter was preferred.

Balancing the anti-microbial efficacy and potential toxicological effects of anti-microbial preservatives is sometimes difficult to achieve. More specifically, the concentration of an antimicrobial agent necessary for the preservation of ophthalmic formulations from microbial contamination may create the potential for toxicological effects on the cornea and/or other ophthalmic tissues. Using lower concentrations of the anti-microbial agents generally helps to reduce the potential for such toxicological effects, but the lower concentrations may be insufficient to achieve the required level of biocidal efficacy (i.e., antimicrobial preservation). The use of an inadequate level of antimicrobial preservation may create the potential for microbial contamination. This balance between anti-microbial efficacy and potential toxicological effects of anti-microbial preservatives is additionally complicated by the fact that many anti-microbial preservatives are ineffective when used in conjunction with some pharmaceutical excipients and/or some pharmaceutical therapeutic agents. For example, some preservatives are rendered less effective when used in conjunction with negatively charged therapeutic agents or excipients.

Since most ophthalmic solutions are prepared in multiple use containers they must be preserved to prevent microbial contamination during storage and duration of use. Preservatives and antimicrobial agents suitable for use include, but are not limited to, thimerosal, benzalkonium chloride, benzalkonium chloride, edentate disodium, methyl and propyl paraben, benzyl alcohol, benzyl dodecinium bromide and phenylthanol, boric acid. It is necessary to demonstrate that the efficacy of the antimicrobial preservation in the ophthalmological solution is sufficient, however, the quantity of the preservatives used should be the minimum required as not to be harmful to the patient. The present invention demonstrates that benzalkonium chloride, exhibits adequate microbial preservation and is also safe for administration to patients. In the present invention the antimicrobial efficacy is demonstrated according to the European Pharmacopoeia guidelines (5.0; 01/2005:50103).

The aqueous formulation according to the present invention comprises from 0.001% to 0.006% (w/v) of benzalkonium chloride, preferably from 0.002% to 0.004% (w/v) of benzalkonium chloride and most preferably is 0.0035% (w/v).

Antioxidants may be required in ophthalmic solutions for selected active agents. Antioxidants include, but are not limited to, thiourea, sodium bisulfide, ethylenediaminetetraacetic acid, vitamin E tocopherol polyethylene glycol succinate.

The compositions of the present invention may contain various other types of pharmaceutical excipients, such as surfactants, viscosity-modifying agents and so on. The present invention has been found particularly advantageous for forming ophthalmic aqueous suspensions, particularly therapeutic agent suspensions that include an anionic polymer as a viscosity agent or a suspending agent. Examples of anionic polymers include, without limitation, carboxyvinyl polymer, xanthan gum, gelan gum, sodium carboxymethyl cellulose, alginic acid, carageenans. Highly preferred examples of anionic polymers include carboxyvinyl polymer, xanthan gum or a combination thereof. These anionic polymers are typically incompatible with high molecular weight or multicharged cationic preservatives such as Polyquaterniunl. However, these anionic polymers are substantially more compatible with benzalkonium chloride. Notably, prior to the present invention, relatively high concentrations of benzalkonium chloride were typically needed to preserve anionic polymer based suspensions as well as other ophthalmic compositions to Ph. Eur B or Ph. Eur.A criteria.

Typically, carboxyvinyl polymer will have a network of cross-linked polymer chains. The polymers are often characterized as having carboxylic acid functional groups and preferably contain from 2 to 7 carbon atoms per functional group. Preferred carboxyvinyl polymers include water-soluble and water-swellable carbomers, available under the trade name CARBOPOL from Lubrizol. The commercially available polymers Carbopol 934P, 940 and 974P are highly preferred. The amount of carboxyvinyl polymer present in the pharmaceutical composition of the present invention is typically at least about 0.05%, more typically at least about 0.1% even more typically at least about 0.2%.

Moreover, the amount of carboxyvinyl polymer present in the pharmaceutical composition of the present invention is typically less than about 4.0%, more typically less than about 1.0% even more typically less than about 0.5%.

For suspension, particularly those that include carboxyvinyl polymers as a suspending agent, it is desirable for the viscosity of the suspensions to be sufficiently high to keep a therapeutic agent suspended for a substantial period of time. The viscosity of the suspension is typically greater than 5 cps, more typically greater than 70 cps and even more typically greater than 125 cps. The viscosity of the suspension is typically less than 1000 cps, more typically less than 700 cps. The viscosity of the suspension is measured using Brookfield viscometer (30 rpm, spindle 31) It is also desirable for such suspension to have osmolality in the range of 240 to 360 mOsm. In one embodiment, sodium chloride is used to adjust the tonicity in addition to borate-polyol. When sodium chloride is used, the concentration of sodium chloride is typically high enough to achieve the desired osmolality but less than 0.9%, more typically less than 0.6% and even more typically less than 0.4% since sodium chloride can negatively impact the viscosity of the suspension for at least some compositions.

When the composition of the present invention is a suspension, it is typically desirable that the therapeutic agent of the suspension be easily re-dispersed. Suspensions according to the present invention can typically be re-dispersed with no more than 30 seconds, more typically no more than 20 and even more typically no more than 15 seconds of vigorous shaking.

A surfactant may be used e.g., as a wetting agent in a suspension or as a solubilizer or as a stabilizer. The preferred surfactants are tyloxapol, Poloxamer, polysorbate 80 and Polyoxyethylene (POE) (40) Hydrogenated Castor oil (or PEG (40 Hydro-genated castor oil) (HCO-40). When used, the concentration of thee surfactant is typically sufficient to achieve a desired degree of wetting by is less than 1.0%, more typically less than 0.5% and even more typically less than 0.1%.

As an advantage of the present invention, it is believed that the lower concentrations of BAC within the compositions of the present invention allow the compositions to be more suitable for repeated administrations to the eye. This is achieved due to the combination of the polyol-borate system and the amount of BAC in the composition. There are multiple eye disorders such as elevated intraocular pressure (IOP) for which the desired treatment is repeated administration of the composition to the eye for an extend period of time. Thus, once the eye[s] have been diagnosed with such a disorder, chronic treatment of the disorder typically involves repeated administration of a composition to the eye[s]. In such treatment, the composition can be administered at least once a week, more typically at least once a day and even possibly at least twice or three times a day for a period of at least one month, more typically at least six months and even more typically at least one year. The compositions are believed to be quite suitable for such treatment.

An increase in the viscosity of ophthalmic solutions will result in a longer resident time in the eye, providing a longer time for absorption and effect. Most common viscosity enhancers are, but are not limited to, methylcellulose, hydroxypropyl methylcellulose, polyvinyl alcohol, polyvinylpyrrolidine.

The present invention can be directed to the provision of multi-dose ophthalmic compositions in connection with the treatment of conditions wherein the cornea or adjacent ocular tissues are irritated, or conditions requiring frequent application of a composition, such as in the treatment of dry eye patients. The compositions of the present invention can be useful in the field of artificial tears, ocular lubricants, and other compositions used to treat dry eye conditions, as well as other conditions involving ocular inflammation or discomfort. The compositions may also be particularly useful for treating glaucoma.

The compositions of the present invention will generally be formulated as sterile aqueous solutions or suspension. The compositions of the present invention are also formulated so as to be compatible with the eye and/or other tissues to be treated with the compositions. The ophthalmic compositions intended for direct application to the eye will be formulated so as to have a pH and tonicity that are compatible with the eye. It is also contemplated that the compositions can be suspensions or other types of solutions.

The present invention is particularly directed to the provision of multi-dose ophthalmic compositions that have sufficient antimicrobial activity to allow the compositions to satisfy the USP preservative efficacy requirements, as well as other preservative efficacy standards for aqueous pharmaceutical compositions.

Finally, common ophthalmic drugs are also suitable for use in the composition or the present invention which include, but are not limited to, chloramphenicol, timolol, dorzolamide, travoprost, bimatoprost, latanoprost, prednisolone, levobunolol, levofloxacin, moxifloxacin, dexamethasone, apraclonidine, bromfenac, epinastine, loteprednol, pegaptanib, prednisolone, pranoprofen, ranibizumab, rimexolone, trafluprost, thiomersal, betaxolol, brimonidine, carteolol, pilocarpine, brinzolamide, apraclonidine, atropine, azelastine, bepotastine, betaxolol, bromfenac, ciprofloxacin, diclofenac, emedastine, epinastine, flurbiprofen, gentamycin, gramicidin, framycetin sulphate, cetrimide, hamamelis water, naphazoline, homatropine, ketorolac trometamol, ketotifen fumarate, levobunolol, lodoxamide trometamol, moxifloxacin, naphazoline, pheniramine maleate, nedocromil sodium, ofloxacin, olopatadine, tetracaine, tetrahydrozoline, tobramycin, xylometazoline, antazoline and combinations such as travoprost/timolol, brinzolamide/brimonidine, dorzolamide/timolol, bimatoprost/timolol, brimonidine/timolol, latanoprost/timolol, brinzolamide/timolol.

The aqueous ophthalmic formulation of the present invention is packaged in a container equipped with a dropper, to facilitate application to the eye. Containers suitable for drop-wise application are usually made of suitable inert, non-toxic material, and generally contain between 0.5 and 15 ml solution. The preferred container for the present invention is a 5 ml polypropylene bottle containing 2.5 ml solution with a low density polyethylene dispensing plug and a white high density polyethylene closure and a foil overwrap.

The following examples illustrate a preferred embodiment in accordance with the present invention, without limiting the scope or the spirit of the invention.

EXAMPLES

Example 1

The inventors tested different combinations of a polyol-borate system and decided to continue with two different polyols. Propylene glycol and mannitol were chosen for two different tests as a single polyol and boric acid was chosen as a borate for both tests. The combinations both resulted in very high antimicrobial protection with the minimum amount of the benzalkonium chloride in the formulation. Four different compositions were tested to determine the optimum quantitative combination. The compositions tested are shown below in Table 1. Each of the compositions 1A to 1D includes Carbomer 974P for increasing viscosity. All compositions meet Ph. Eur. A/B criteria. These compositions can be used for ophthalmic suspensions of drugs such as brinzolamide, brimonidine, prednisolone, dexamethasone and loteprednol, nepafenac, bradykinin inhibitor, combinations thereof and their combinations with other drugs.

All compositions had adequate antimicrobial activity in tests for up to 6 months and at temperatures up to 40° C. Composition 1B showed the best physicochemical characteristics and therefore it was further tested in stability studies shown in Table 2 showing that the composition remains stable.

TABLE 1

Quantitative and qualitative analysis of compositions 1A-D

| | Composition | | | |
| | Composition 1A | Composition 1B | Composition 1C | Composition 1D |
| | | % w/v | | |
| Brinzolamide | 1.000 | 1.000 | 1.000 | 1.000 |
| Brimonidine tartarate | 0.200 | 0.200 | 0.200 | 0.200 |
| Benzalkonium Chloride (50%) | 0.0051 | 0.0059 | 0.0059 | 0.0059 |
| Carbomer 974P | 0.430 | 0.430 | 0.430 | 0.430 |
| Boric acid | 0.300 | 0.300 | 0.300 | 0.300 |
| Tyloxapol | 0.025 | 0.025 | 0.025 | 0.025 |
| Propylene glycol | 1.000 | 0.750 | 1.000 | 0.25 |
| Sodium chloride | 0.230 | 0.230 | 2.00 | 0.460 |
| Sodium Hydroxide | | q.s. to adjust pH to 6.50 | | |
| Hydrochloric acid | | q.s. to adjust pH to 6.50 | | |
| Water for Injection | | q.s. to 100 ml | | |
| Osmolality | 295 | 258 | 284 | 262 |
| Viscosity (cps) @30 RMP | 197 | 212 | 198 | 152 |
| pH | 6.55 | 6.53 | 6.53 | 6.50 |

TABLE 2

Chemical stability data for composition 1B
Comp 1B

| | Zero time | 25° C. 6 months | 40° C. 6 months |
|---|---|---|---|
| Assay Brinzolamide | 103.2 | 103.1 | 102.8 |
| Assay Brimonidine | 98.7 | 98.4 | 97.7 |

TABLE 2-continued

Chemical stability data for composition 1B
Comp 1B

| | Zero time | 25° C. 6 months | 40° C. 6 months |
|---|---|---|---|
| Impurities Brinzolamide | 0.17 | 0.22 | 0.40 |
| Impurities Brimonidine | 0.30 | 0.37 | 0.71 |
| Enantiomer Impurity Brinzolamide | 0.03 | 0.08 | 0.60 |

The process for manufacturing the aqueous ophthalmic composition 1B comprising a combination of Brinzolamide or pharmaceutically acceptable salts thereof and Brimonidine or pharmaceutically acceptable salts thereof; in combination with propylene glycol, boric acid, carboxyvinyl polymer, tyloxapol and an appropriate amount of benzalkonium chloride comprises the following steps:

Adding 90% of total amount of water for injection in a clean glass vessel;

Adding sodium chloride and stirring until complete dissolution;

Adding propylene glycol and stirring until complete dissolution;

Adding boric acid and stirring until complete dissolution;

Adding Brizolamide or a pharmaceutically acceptable salt thereof and stirring until complete dissolution Adding Brimonidine or a pharmaceutically acceptable salt thereof and stirring until complete dissolution Adding a carboxyvinyl polymer and tyloxapol and stirring until complete dissolution, Adding Benzalkonium chloride and stirring until complete dissolution If necessary, adjusting pH to 6.50 with HCl/NaOH Adjusting the final volume with water for injection;

Filtering the final solution through a 0.2 am PVDF filter;

Filling and sealing of the final solution in polypropylene vials

Example 2

Four more compositions were tested comprising mannitol as the single polyol in combination with boric acid as the borate. This combination also results in very high antimicrobial protection with the minimum amount of the benzalkonium chloride in the formulation. The compositions tested are shown below in Table 3. Each of the compositions 2A to 2D includes Carbomer 974P for increasing viscosity. All compositions meet Ph. Eur. A/B criteria. These compositions can be used for ophthalmic suspensions of drugs such as brinzolamide, brimonidine, prednisolone, dexamethasone and loteprednol, nepafenac, bradykinin inhibitor, combinations thereof and their combinations with other drugs.

TABLE 3

Quantitative and qualitative analysis of compositions 2A-D

| | Composition | | | |
| | Composition 2A | Composition 2B | Composition 2C | Composition 2D |
| | | % w/v | | |
| Brinzolamide | 1.000 | 1.000 | 1.000 | 1.000 |
| Brimonidine tartarate | 0.200 | 0.200 | 0.200 | 0.200 |
| Benzalkonium Chloride (50%) | 0.0054 | 0.0054 | 0.0059 | 0.0059 |

TABLE 3-continued

Quantitative and qualitative analysis of compositions 2A-D

| | Composition | | | |
|---|---|---|---|---|
| | Composition 2A | Composition 2B | Composition 2C | Composition 2D |
| | | | % w/v | |
| Carbomer 974P | 0.430 | 0.430 | 0.430 | 0.430 |
| Boric acid | 0.300 | 0.600 | 0.300 | 0.300 |
| Tyloxapol | 0.025 | 0.025 | 0.025 | 0.025 |
| Mannitol | 3.3 | 3.3 | 3.3 | 1.5 |
| Sodium chloride | NA | NA | 0.32 | 0.32 |
| Sodium Hydroxide | | q.s. to adjust pH to 6.50 | | |
| Hydrochloric acid | | q.s. to adjust pH to 6.50 | | |
| Water for Injection | | q.s. to 100 ml | | |
| Osmolality | 218 | 231 | 260 | 251 |
| Viscosity (cps) @30 RMP | 210 | 199 | 225 | 178 |
| pH | 6.51 | 6.5 | 6.54 | 6.48 |

All compositions had adequate antimicrobial activity in tests for up to 6 months and at temperatures up to 40° C. It is clear that composition 2C shows the best physicochemical characteristics and it was tested further for chemical stability (Table 4).

TABLE 4

Chemical stability data for composition 2C
Comp 2C

| | Zero time | 25° C. 6 months | 40° C. 6 months |
|---|---|---|---|
| Assay Brinzolamide | 104.5 | 104.2 | 104.3 |
| Assay Brimonidine | 99.1 | 98.1 | 99.4 |
| Impurities Brinzolamide | 0.25 | 0.29 | 0.47 |
| Impurities Brimonidine | 0.25 | 0.33 | 0.74 |
| Enantiomer Impurity Brinzolamide | 0.02 | 0.09 | 0.67 |

The process for manufacturing the aqueous ophthalmic composition 2C comprising a combination of Brinzolamide or pharmaceutically acceptable salts thereof and Brimonidine or pharmaceutically acceptable salts thereof; in combination with mannitol, boric acid, carboxyvinyl polymer, tyloxapol and an appropriate amount of benzalkonium chloride comprises the following steps:

Adding 90% of total amount of water for injection in a clean glass vessel;

Adding sodium chloride and stirring until complete dissolution;

Adding mannitol and stirring until complete dissolution;

Adding boric acid and stirring until complete dissolution;

Adding Brizolamide or a pharmaceutically acceptable salt thereof and stirring until complete dissolution Adding Brimonidine or a pharmaceutically acceptable salt thereof and stirring until complete dissolution Adding a carboxyvinyl polymer and tyloxapol and stirring until complete dissolution, Adding Benzalkonium chloride and stirring until complete dissolution If necessary, adjusting pH to 6.50 with HCl/NaOH Adjusting the final volume with water for injection;

Filtering the final solution through a 0.2 μm PVDF filter;

Filling and sealing of the final solution in polypropylene vials

While the present invention has been described with respect to the particular embodiments, it will be apparent to those skilled in the art that various changes and modifications may be made in the invention without departing from the spirit and the scope thereof, as defined in the claims.

The invention claimed is:

1. An aqueous ophthalmic composition consisting of:

Brinzolamide or a pharmaceutically acceptable salt thereof,

Brimonidine or a pharmaceutically acceptable salt thereof, a polyol-borate system consisting of (1) a single polyol selected from the group consisting of glycerine, propylene glycol, sugars, sugar alcohols, sugar acids, and uronic acid, and (2) borate, an antimicrobial preservative, water, optionally at least one viscosity enhancing agent, optionally at least one surfactant, optionally at least one tonicity adjusting agent selected from the group consisting of sodium chloride, potassium chloride, calcium chloride and magnesium chloride, optionally at least one suspending agent selected from carboxyvinyl polymers, optionally at least one antioxidant, and optionally at least one buffering agent, wherein the composition satisfies USP preservative efficacy requirements, wherein the composition contains only one polyol selected from the group consisting of glycerine, propylene glycol, sugars, sugar alcohols, sugar acids, and uronic acid, and wherein the composition has a viscosity of from 210 cps to less than 1000 cps as measured using Brookfield viscometer at 30 rpm, spindle 31.

2. The aqueous ophthalmic composition according to claim 1, wherein the single polyol of the polyol-borate system is selected from the group consisting of mannitol, sorbitol, xylitol, glycerol, and propylene glycol.

3. The aqueous ophthalmic composition according to claim 2, wherein the single polyol is mannitol or propylene glycol.

4. The aqueous ophthalmic composition according to claim 3, wherein a concentration of polyol is from 0.5% to 3.5% w/v.

5. The aqueous ophthalmic composition according to claim 2, wherein a concentration of the single polyol is from 0.5% to 3.5% w/v.

6. The aqueous ophthalmic composition according to claim 1, wherein the borate is selected from the group consisting of boric acid and borate salts.

7. The aqueous ophthalmic composition according to claim 6, wherein the borate is boric acid.

8. The aqueous ophthalmic composition according to claim 7, wherein a concentration of borate is 0.3% w/v.

9. The aqueous ophthalmic composition according to claim 6, wherein a concentration of the borate is 0.3% w/V.

10. The aqueous ophthalmic composition according to claim 1, wherein the antimicrobial preservative is Benzalkonium chloride in a concentration of from 0.003% to 0.004% w/v.

11. The aqueous ophthalmic composition according to claim 1, wherein a surfactant is present in the composition.

12. The aqueous ophthalmic composition according to claim 11, wherein the surfactant is selected from the group consisting of tyloxapol poloxamer, polysorbate 80, polyoxyethylene 40 hydrogenated castor oil, polyethylene glycol 40 hydrogenated castor oil, and mixtures thereof.

13. The aqueous ophthalmic composition according to claim 12, wherein the surfactant is tyloxapol and present in an amount of less than 0.1% w/v.

14. The aqueous ophthalmic composition according to claim 1, wherein a suspending agent is present in the composition.

15. The aqueous ophthalmic composition according to claim 14, wherein the suspending agent is present in an amount of at least 0.4% w/v.

16. The aqueous ophthalmic composition according to claim 1, for use in lowering intraocular pressure in patients with open-angle glaucoma and/or ocular hypertension.

17. The aqueous ophthalmic composition according to claim 1, wherein the borate is selected from the group consisting of sodium borate, potassium borate, calcium borate, magnesium borate, and manganese borate.

18. The aqueous ophthalmic composition according to claim 1, wherein the composition does not contain suspending agent.

19. A process for manufacturing an aqueous ophthalmic composition comprising Brinzolamide or a pharmaceutically acceptable salt thereof, Brimonidine or a pharmaceutically acceptable salt thereof, a polyol-borate system consisting of (1) a single polyol selected from the group consisting of mannitol and propylene glycol and (2) boric acid, a carboxyvinyl polymer, tyloxapol and benzalkonium chloride in an antimicrobially effective amount, wherein the composition satisfies USP preservative efficacy requirements and wherein the composition contains only one polyol selected from the group consisting of mannitol and propylene glycol, comprising:

adding 90% w/v of a total amount of a final solution of water for injection in a clean glass vessel;

Adding sodium chloride and stirring until complete dissolution;

Adding a single polyol and stirring until complete dissolution;

Adding boric acid and stirring until complete dissolution;

Adding Brizolamide or a pharmaceutically acceptable salt thereof and stirring until complete dissolution;

Adding Brimonidine or a pharmaceutically acceptable salt thereof and stirring until complete dissolution;

Adding a carboxyvinyl polymer and tyloxapol and stirring until complete dissolution;

Adding Benzalkonium chloride and stirring until complete dissolution;

If necessary, adjusting pH to 6.50 with HCl/NaOH;

Adjusting solution volume with water for injection;

Filtering the solution through a 0.2um PVDF filter; and

Filling and sealing the final solution in polypropylene vials, wherein the composition has a viscosity of from 210 cps to less than 1000 cps as measured using Brookfield viscometer at 30 rpm, spindle 31.

* * * * *